United States Patent [19]
Stouder, Jr.

[11] Patent Number: 5,234,460
[45] Date of Patent: Aug. 10, 1993

[54] LAPAROSCOPY INSTRUMENT

[76] Inventor: Albert E. Stouder, Jr., Doctors Park, R.R. 4, Tipton, Ind. 46072

[21] Appl. No.: 903,377

[22] Filed: Jun. 24, 1992

[51] Int. Cl.$^5$ .............................................. A61B 17/00
[52] U.S. Cl. .................................. 606/205; 81/177.7; 81/177.8; 81/177.9; 606/1
[58] Field of Search .................... 606/1, 51, 52, 127, 606/205–210, 110, 113, 127; 81/177.7–177.8, 177.9, 316, 343, 344, 346, 393, 406

[56] References Cited
U.S. PATENT DOCUMENTS

| | | |
|---|---|---|
| 652,525 | 6/1900 | Stohlmann et al. . |
| 943,263 | 12/1909 | Moraweck ........................ 606/205 |
| 1,155,937 | 10/1915 | Lerfald ............................. 81/177.8 |
| 1,274,669 | 8/1918 | Bohn . |
| 1,359,164 | 11/1920 | Lo Giudice ....................... 606/205 |
| 1,659,112 | 2/1928 | Littlejohn . |
| 2,113,246 | 4/1938 | Wappler ............................ 606/205 |
| 2,507,710 | 5/1950 | Grosso .............................. 606/205 |
| 2,518,994 | 8/1950 | Miller . |
| 3,709,215 | 1/1973 | Richmond ........................ 606/205 |
| 3,742,957 | 7/1973 | White . |
| 3,866,610 | 2/1975 | Kletschka . |
| 4,712,545 | 12/1987 | Honkanen . |
| 4,898,157 | 2/1990 | Messroghli et al. . |
| 4,945,920 | 8/1990 | Clossick . |
| 4,950,273 | 8/1990 | Briggs . |
| 5,047,046 | 9/1991 | Budoia . |
| 5,171,256 | 12/1992 | Smith et al. ...................... 606/205 |

OTHER PUBLICATIONS

Photocopy of an advertisement for the Endoscopic Grasping Forceps, manufactured by Richard Wolf.

Primary Examiner—Stephen C. Pellegrino
Assistant Examiner—Glenn Dawson
Attorney, Agent, or Firm—Woodard, Emhardt, Naughton, Moriarty & McNett

[57] ABSTRACT

An instrument for use in laparoscopy in which the handles are swept back and angled downwardly to provide an ergonomically improved device. The improved handle assembly includes two handle portions. The proximal end of each handle diverges away from the longitudinal axis of the instrument so that from a top plan view the first and second handles lie substantially on opposite sides of that longitudinal axis. The proximal ends of the handles are angled downwardly so that the plane defined by the proximal ends of the handles is non-parallel with respect to the longitudinal axis. The proximal ends of the first and second handle portions optionally are adjustably angled downwardly between about 5° and about 60° with respect to the longitudinal axis when viewed from a side elevational view. An interchangeable sheath holder having tapered sides, and an index finger guide/rest are also disclosed.

19 Claims, 5 Drawing Sheets

LAPAROSCOPY INSTRUMENT

BACKGROUND OF THE INVENTION

This invention relates generally to medical instruments for use in laparoscopy, and more particularly to an ergonomically improved laparoscopy device which provides greater comfort, control and stability relative to such instruments of the prior art.

A variety of medical instruments are used in laparoscopy. Laparoscopic forceps, clamps and scissors are examples of such instruments. In many laparoscopic instruments, the operative portion of the instrument, typically located at the distal end of the instrument is actuated by a cable or wire slidably positioned within a sheath and controlled by a pair of handles. The handles are typically arranged such that one handle member secures and holds the sheath, while another handle member provides reciprocal movement of the cable or wire.

In the instruments of the prior art, one or more of the handles are typically positioned perpendicularly to the longitudinal axis of the instrument. Because the laparoscopy instrument is being directed into a vertically disposed cannula during laparoscopic procedures, traditional laparoscopic handles force the doctor to operate the instrument with his arm held at an awkward angle, the elbow thrust upward. Because laparoscopic procedures may take several hours to perform, such positioning of the handles may cause a reduction in precise control of the instrument and/or unnecessary fatigue in the operator.

A need therefore exists for a laparoscopy instrument which is ergonomically improved and allows for its operation while the operator's arms are more comfortably positioned. The present invention solves this need.

SUMMARY OF THE INVENTION

Briefly describing the present invention, there is provided an instrument for use in laparoscopy in which the handles are swept back and angled downward to provide an ergonomically improved device. The improved handle assembly includes two handle portions. The proximal end of each handle diverges away from the longitudinal axis of the instrument so that from a top plan view the first and second handles lie substantially on opposite sides of that longitudinal axis. The proximal ends of the handles are also angled downwardly so that the plane defined by the proximal ends of the handles is non-parallel with respect to the longitudinal axis. The proximal ends of the first and second handle portions optionally are adjustably angled downwardly between about 5° and about 60° with respect to the longitudinal axis when viewed from a side elevational view. An interchangeable sheath holder having tapered sides, and an index finger guide/rest are also disclosed.

One object of the present invention is to provide an ergonomically improved laparoscopic device.

Related objects and advantages of the present invention will be apparent from the following description.

DESCRIPTION OF THE PREFERRED EMBODIMENT

For the purposes of promoting an understanding of the principles of the invention, reference will now be made to the preferred embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated herein, being contemplated as would normally occur to one skilled in the art to which the invention relates.

The present invention relates to an instrument for use in laparoscopy in which the handles are swept back and angled downwardly to provide an ergonomically improved device.

Figure 1:
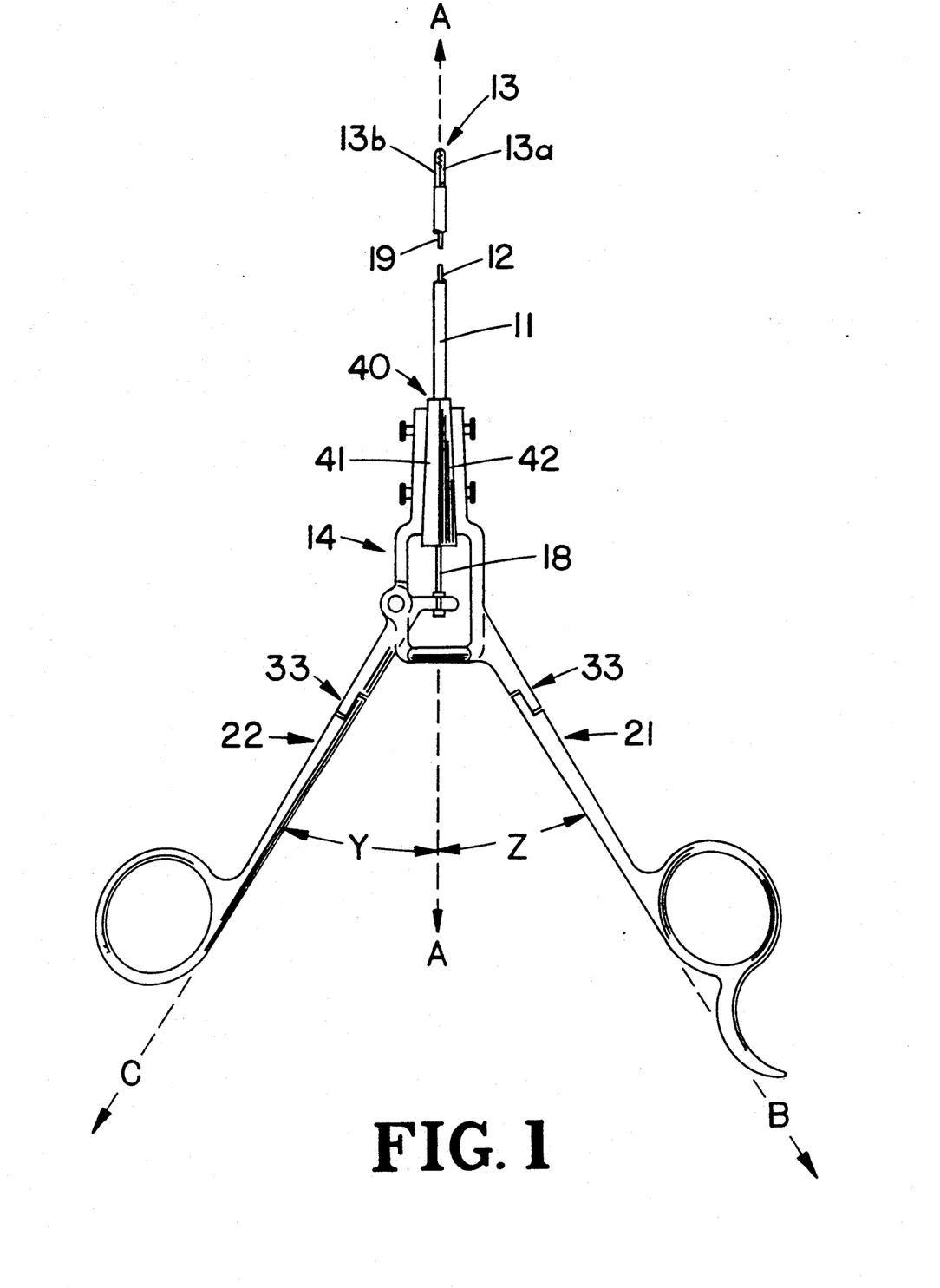
FIG. 1 is a top plan view of the laparoscopy device of the present invention according to one embodiment.
Figure 2:
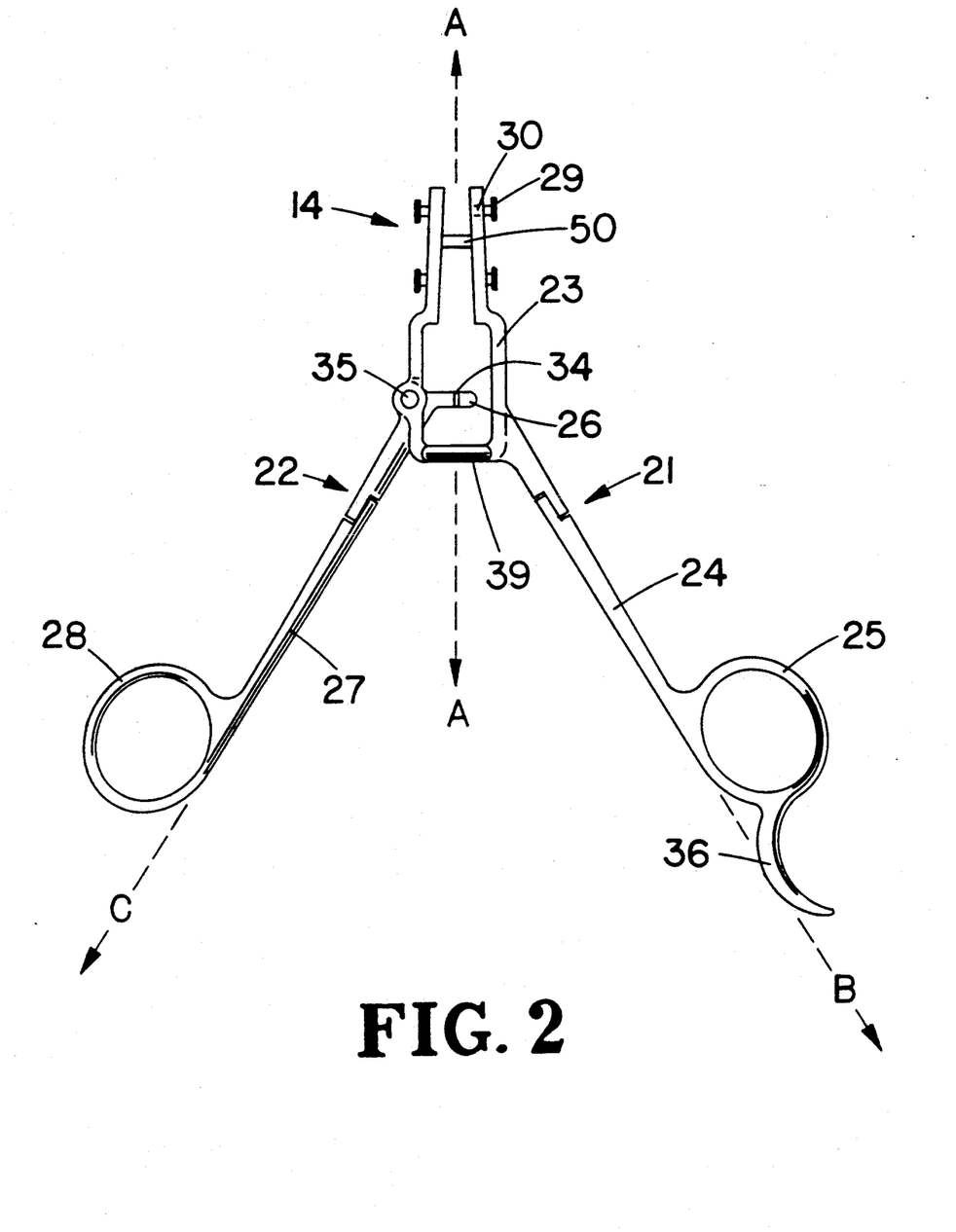
FIG. 2 is a top plan view of the handle assembly of the device of FIG. 1.
Figure 3:
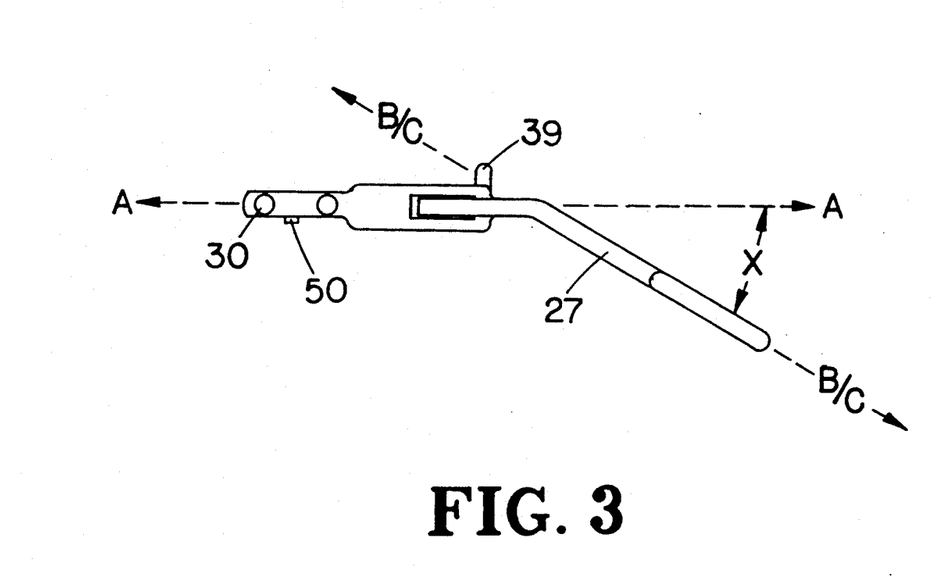
FIG. 3 is a side elevational view of a second embodiment of the laparoscopy device of the present invention with fixed downwardly angled proximal end portions of the handles.
Figure 4:
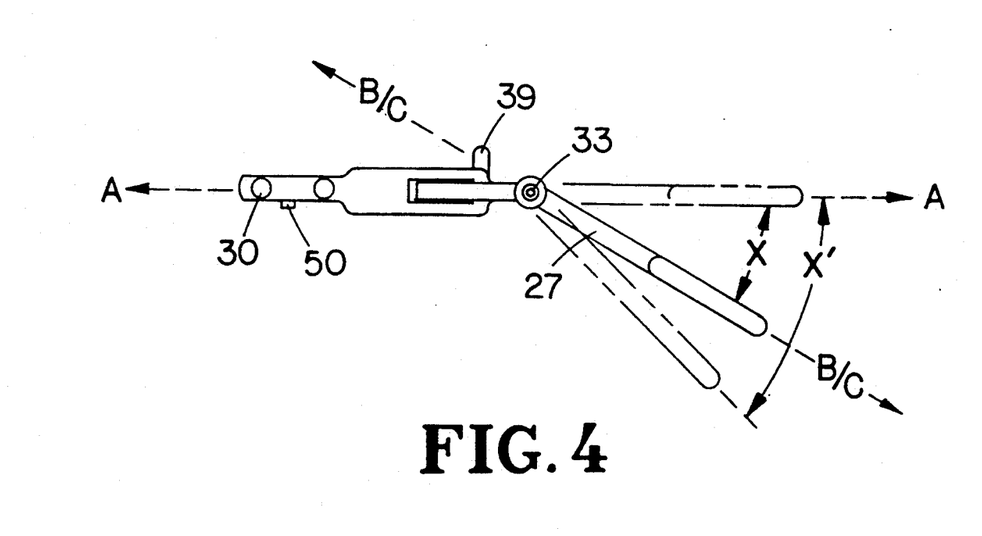
FIG. 4 is a side elevational view of the handle assembly of the device of FIG. 2.
Figure 5:
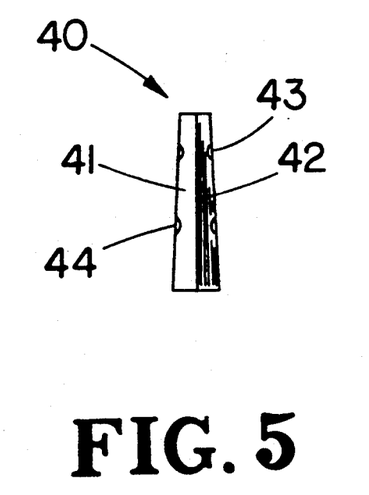
FIG. 5 is a top plan view of one embodiment of the universal adaptor of the present invention.
Figure 6:
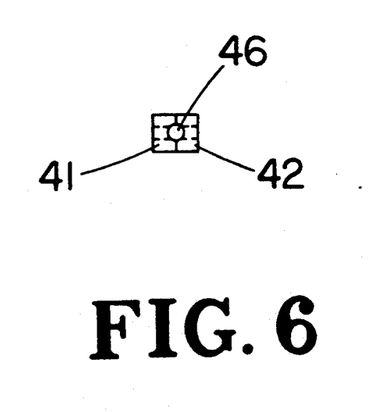
FIG. 6 is an end view of the adaptor of FIG. 5 showing the lateral holes in phantom lines.
Figure 7:
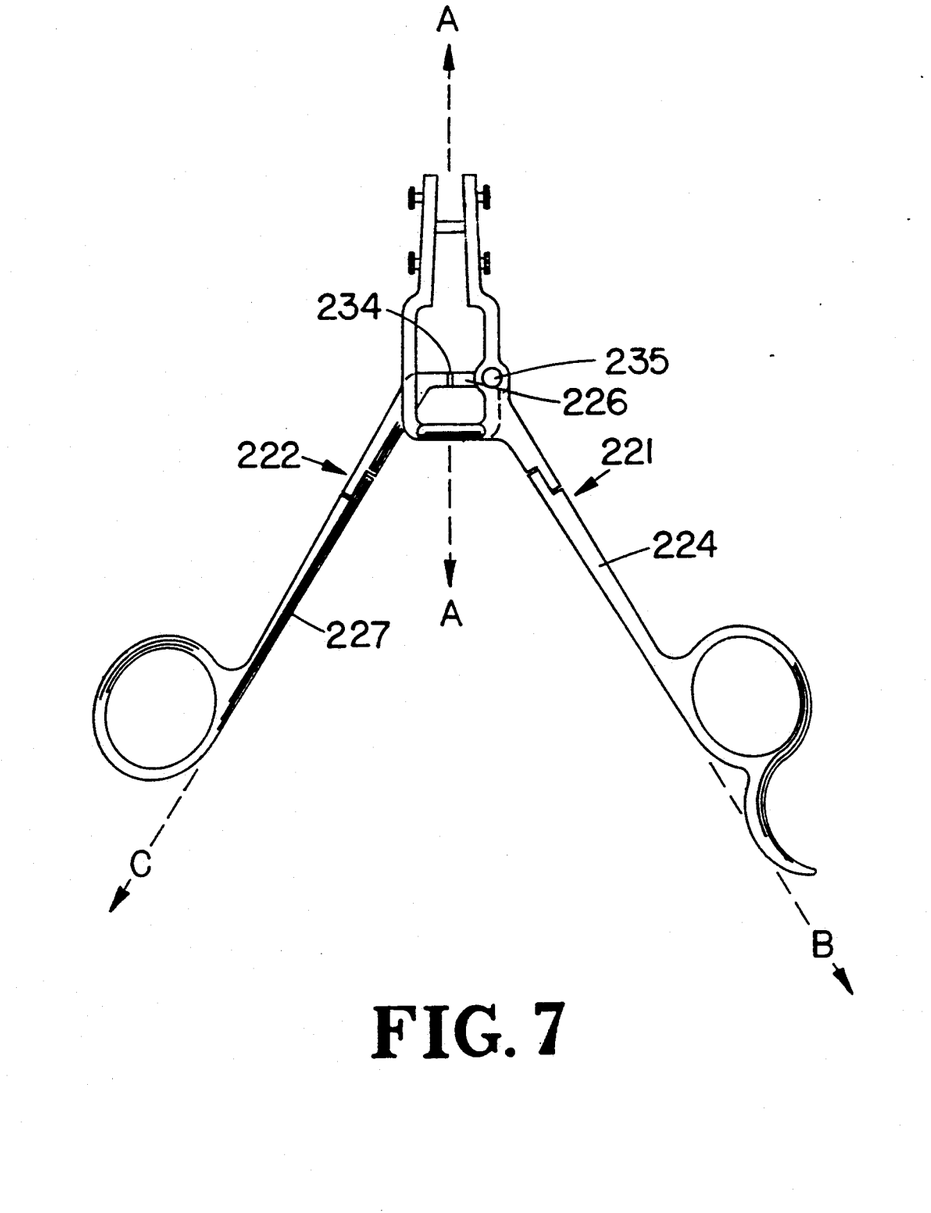
FIG. 7 is a top plan view of the handle assembly of the present invention, according to one alternative embodiment.

Referring now to the drawings, FIGS. 1, 2 and 4 illustrate the laparoscopy device according to one preferred embodiment, while FIGS. 3 and 7 illustrate alternative embodiments of the device. FIGS. 5 and 6 illustrate the universal adaptor of the present invention.

Laparoscopy instrument 10 includes an elongated sheath 11 which serves as a conduit for an actuating wire 12 attached to a clamp 13 for grabbing, retrieving or other related function. Sheath 11 is secured to a handle assembly 14. Actuating wire 12 is slidably disposed in sheath 11. The proximal end portion 18 of actuating wire 12 is attached to handle assembly 14 at handle 22, while the distal end portion 19 of wire 12 is attached to clamp 13. The arrangement is such that when the handle assembly is operated, actuating wire 12 moves reciprocally in sheath 11 and causes a responsive opening and closing movement of clamp 13. This responsive movement pivots at least one jaw of clamp 13 and thereby opens or closes jaw 13a with respect to jaw 13b of the clamp as is known in the art.

Handle assembly 14 includes a first handle member 21 and a second handle member 22. First handle member 21 includes a distal end portion 23 and a proximal end portion 24 (see FIG. 2). Proximal end portion 24 preferably includes finger loops or rests for establishing a more secure grip on the handle. In preferred embodiments, this comprises a finger loop 25 and finger rest 36, as shown in the figures.

The distal end portion 23 of first handle member 21 includes a mechanism for releasably securing sheath 11 to the handle assembly. In preferred embodiments, this securing is accomplished by one or more screws 29 passing through threaded apertures 30 in portion 23. Other structures may be used as well, including snap-in, push-in, friction-fit and other securement. This securing allows longitudinal and rotational movement of the sheath and the tool at its end (e.g., clamp 13) by wrist movement of handle 21.

Second handle member 22 includes a distal end portion 26 and a proximal end portion 27 (see FIG. 2). Here too, proximal end portion 27 preferably includes finger loops or rests for providing a more secure grip on the handle, such as finger loop 28.

The second handle member also includes means for releasably securing the proximal end 18 of actuating wire 12. In preferred embodiments, said securing means comprises snap-in slot 34 into which the end of wire 12 can be fit. The end of the wire has a stop member, such as the spool-shaped stop illustrated, affixed to it to prevent longitudinal slippage between the distal end 26 of the handle and the wire.

First handle member 21 and second handle member 22 are preferably pivotably connected with a pin 35 (see FIG. 2) through their respective distal end portions. This connection allows the second handle member 22 to move relative to first handle member 21 in a manner which moves the distal end portion 26 of second handle member 22. This movement of distal end portion 26 reciprocally moves actuating wire 12 in sheath 11, thereby responsively moving at least one of the clamp jaws.

Sheath 11 defines a longitudinal axis A—A (see FIGS. 1-4), and handle assembly 14, most particularly its distal end portion 23, also is aligned along that axis. Handle 22 defines axis C therealong and handle 21 defines axis B therealong as illustrated in FIG. 1. The ergonomic use of the laparoscopy instrument is improved by positioning the first and second handle members, 21 and 22 respectively, substantially on opposite sides of that longitudinal axis when the instrument is viewed from a top plan view (see FIGS. 1 and 2). In particular, it can be seen that first handle member 21 and second handle member 22 diverge away from the longitudinal axis so that the proximal end portions, 24 and 27, are positioned on opposite sides of the longitudinal axis. This creates a "swept back" arrangement of the handle assembly and allows the operator to manipulate the instrument in a more comfortable manner. This is accomplished by having the angle Y formed between axis A and axis C (of handle 22) preferably be less than or equal to 45°; and, having the angle Z formed between axis A and axis B (of handle 21) preferably also be less than or equal to 45°.

In another aspect of the invention, the proximal end portions of the handle assembly are angled downwardly from the plane of the distal end portions. As illustrated in FIGS. 3 and 4, the proximal end portions of the handles are angled downwardly so that the plane B/C defined by axis B and axis C and the proximal ends of the handle members is non-parallel with respect to the longitudinal axis. The plane B/C forms an angle X and/or X' of between about 5° and about 60° with respect to longitudinal axis A when viewed from a side elevational view (see FIGS. 3 and 4). This handle configuration provides a further ergonomic improvement to the laparoscopy instrument, particularly when used in conjunction with the swept back handle feature described above, allowing ease of manipulation by wrist movement alone.

In the instrument illustrated in FIG. 3 the proximate ends of the handles are angled downwardly in a fixed, non-adjustable position. In the other embodiment (see FIG. 4) the proximate ends of the handles are adjustably angled downwardly. In adjustable embodiments the downward angles of the proximal end portions of the handle members are preferably adjustable to angles of between about 0° and about 60° with respect to the instrument's longitudinal axis from a side elevational view. Accordingly, handle members 21 and 22 each preferably include means for adjustably angling the proximal end portions of the handle members downwardly. As is shown in FIG. 4, such angle adjusting means may comprise an allen wrench set screw 33 as illustrated. Other structures such as ratcheted or friction-fit systems may be used.

It is to be appreciated that the laparoscopy instrument is typically used with the operator s thumb in loop 28 of second handle member 22 and the operator's fingers in loop 25 and finger rest 36 of first handle member 21. The operator's fine motor control over the instrument is further improved by including means for controlling the distal end of the device. Accordingly, an index finger guide/support 39 is provided on the handle assembly. When using the instrument, the operator places his thumb and fingers in the appropriate finger loops and/or rests as described above and also places his index finger on the index finger guide/support. This not only improves the ergonomic characteristics of the instrument, but it also enhances the ability of the operator to precisely guide and control the distal end of the device. Thus, both the ergonomic comfort and the fine instrument control of the operator are improved by the index finger guide/support of the present invention.

In a further aspect of the invention, a universal adaptor is included to allow the ergonomic handle assembly to be used with a wide variety of sheath members, and with sheath members having a variety of diameters. As is shown in FIGS. 5 and 6, universal adaptor 40 comprises two adaptor members, 41 and 42, each of which includes one or more apertures, 43 and 44, to receive screws 29. The inner surfaces of the adaptor members 41 and 42 define an elongated longitudinal aperture 46 (see FIG. 6) when the adaptor members are positioned together. This elongated longitudinal aperture 46 surrounds and grips the sheath member, holding the sheath member in a fixed position relative to first handle member 21.

The universal adaptor is secured by screws 29 to the distal end portion of first handle member 21 and contacts the proximal end of the sheath member to removably secure the sheath/wire assembly to the handles. When a sheath member having a large outer diameter is used, the two adaptor halves may not contact each other when screws 29 are tightened. When smaller diameter sheaths are used however, the two adaptor halves may come into contact with each other. In all cases, a snug fit with the sheath member is assured.

The outer profile of the universal adaptor is trapezoidal, tapering towards its distal end. This shape provides improved stability of the adaptor in the handle assembly and prevents the adaptor from being pulled out of the handle or otherwise dislodged while the instrument is being used.

Because a variety of wire guides and other wire-actuated tools are available, the universal adaptor allows the ergonomic handle assembly to operate a wide variety of such devices. Accordingly, one aspect of the invention comprises the ergonomic handle assembly alone, without any specific wire-actuated device attached. The selection of an appropriate wire-actuated tool for use with the ergonomic handles can be accomplished. It is therefore to be appreciated that the ergonomic handle assembly of the present invention may be used with a variety of laparoscopic instruments. Thus, although the illustrated embodiment comprises a laparoscopic clamp, it can be seen that laparoscopic forceps, cutters, retrieval systems and others may also be provided.

In addition, alternative embodiments of the present invention may accommodate tools that are actuated by pulling, rather than pushing, a reciprocating member. In such embodiments (see FIG. 7) the means for releasably securing the proximal end of the actuating wire is located between pivot 235 and the proximal end 227 of second handle member 222 rather than between pivot 235 and the distal end 226 of the second handle member 222. In preferred embodiments, said securing means again comprises snap-in slot 234 into which the end of a wire can be fit.

In this alternative embodiment, the pivot 235 which pivotably connects first handle member 221 and second handle member 222 is preferably a pin passing through the two handle members. Therefore, as was shown in the first-described embodiment, second handle member 222 may be moved relative to first handle member 221 in a manner which reciprocally moves the actuating wire, thereby responsively moving at least one of the clamp jaws. However because the fulcrum of the lever provided by second handle member 222 has been moved to the opposite side of the load, compared to the embodiment shown in FIGS. 1-4, a movement of second handle member 222 toward first handle member 224 serves to pull, rather than push, the reciprocating member in its sheath.

When using this alternative embodiment it is preferred to insert universal adaptor 40 in the handle assembly so that the adaptor is resistant to being pulled toward the proximal end of the handles. Accordingly, with a trapezoidally shaped adaptor, the longer parallel side is preferably at the distal end of the instrument.

A stabilizing bar 50 may also be included near the distal end of the instrument. This bar resists twisting and torquing forces imposed on the instrument during medical procedures. In addition, the stabilizing bar prevents the distal end portion members from spreading apart when screws 29 are tightened on universal adaptor 40.

A number of variations are contemplated to be within the scope of applicant s invention and may be included to adapt the device to a particular use without changing the basic features. Therefore, while the invention has been described in detail in the foregoing description of the preferred embodiment, this description is to be considered illustrative and not restrictive in character. It is to be understood that only the preferred embodiments have been shown and described, and that all changes and modifications within the spirit of the invention are desired to be protected.

What is claimed is:

1. An instrument for use in laparoscopy, comprising:
   (a) an elongated sheath member sized to be inserted through a laparoscope instrument and having a distal end and a proximal end, said sheath member defining a longitudinal axis;
   (b) a movable member at the distal end of said sheath member and sized to be inserted through a laparoscope instrument;
   (c) a reciprocating member connected to said movable member and sized to be inserted through a laparoscope instrument, having a distal end and a proximal end, to cause responsive movement of said movable member; and
   (d) a handle assembly at the proximal end of said sheath member, said handle assembly including;
      (i) a first handle member attached to said sheath member;
      (ii) a second handle member, movable with respect to the first handle member and attached to the proximal end of said reciprocating member to cause reciprocal movement of said reciprocating member when the second handle member is moved relative to the first handle member; wherein
   the first member and the second handle member diverge away form the longitudinal axis so that from a top plan view the first handle member and the second handle member lie substantially on opposite sides of the longitudinal axis, and wherein the first handle member and the second handle member are further angled downwardly so that a plane is defined by the handle members which s non-parallel with respect to the longitudinal axis and which forms an angle of between about 5° and about 60° with respect to the longitudinal axis when viewed from a side elevational view.

2. The instrument of claim 1 wherein angles formed between the longitudinal axis and the handle members are less than about 45° when viewed from a top plan view.

3. The instrument of claim 2 wherein the first handle member and the second handle member of said handle assembly are arranged in substantial symmetry with respect to the longitudinal axis when viewed from a top plan view.

4. The instrument of claim 3 wherein the second handle member is pivotably movable with respect to the first handle member.

5. The instrument of claim 4 and further including means for releasably fixing said sheath member to said handle assembly.

6. The instrument of claim 5 wherein said means for releasably fixing said sheath member to said handle assembly is adapted to accept various sheath members having various outer diameters.

7. The instrument of claim 6 wherein the handle assembly further includes an index finger supporting member.

8. The instrument of claim 1 wherein the first handle member and the second handle member of said handle assembly are arranged in substantial symmetry with respect to the longitudinal axis when viewed from a top plan view.

9. The instrument of claim 1 wherein the second handle member is pivotably movable with respect to the first handle member.

10. The instrument of claim 1 and further including means for releasably fixing said sheath member to said handle assembly.

11. The instrument of claim 10 wherein said means for releasably fixing said sheath member to said handle assembly is adapted to accept various sheath members having various outer diameters.

12. The instrument of claim 1 wherein the handle assembly further includes an index finger supporting member.

13. An instrument for use in a laparoscopy, comprising:
   (a) an elongated sheath member sized to be inserted through a laparoscope instrument and having a distal end and a proximal end, said sheath member defining a longitudinal axis;

(b) a movable member located at the distal end of said sheath member and sized to be inserted through a laparoscope instrument;

(c) a reciprocating member connected to said movable member and sized to be inserted through a laparoscope instrument, having a distal end and a proximal end, to cause responsive movement of said movable member; and (d) a handle assembly at the proximal end of said sheath member, said handle assembly including;

(i) a first handle member, having a distal end and a proximal end, the distal end being attached to said sheath member;

(ii) a second handle member, having a sheath end and a proximal end, movable with respect to the first handle member, the distal end of the second handle member being attached to the proximal end of said reciprocating member to cause reciprocal movement of said reciprocating member when the second handle member is moved relative to the first handle member; wherein the first handle member and the second member each include means for selectively pivoting their respective proximal ends downwardly with respect to the longitudinal axis, so that the proximal ends of the handle members may each be adjustably positioned at a variety of angles between about 0° and about 60° with respect to the longitudinal axis when viewed from a side elevational view.

14. The instrument of claim 13 wherein the first handle member and the second handle member of said handle assembly are arranged in substantial symmetry with respect to the longitudinal axis when viewed from a top plan view.

15. The instrument of claim 14 wherein the second handle member is pivotably movable with respect to the first handle member.

16. The instrument of claim 15 and further including means for releasably fixing said sheath member to said handle assembly.

17. The instrument of claim 16 wherein said means for releasably fixing said sheath member to said handle assembly is adapted to accept various sheath members having various outer diameters.

18. The instrument of claim 17 wherein the handle assembly further includes an index finger supporting member.

19. An instrument for use in laparoscopy, comprising:

(a) an elongated sheath member sized to be inserted through a laparoscope instrument and having a distal end and a proximal end, said sheath member defining a longitudinal axis;

(b) a handle assembly at the proximal end of said sheath member, said handle assembly including;

(i) a fist handle member, attached to said sheath member;

(ii) a second handle member, movable with respect to the first handle member and attached to a reciprocating member to cause a responsive movement of said reciprocating member when the second handle member is moved relative to the first handle member; and (c) an adaptor comprising a first adaptor member and a second adaptor member to secure said sheath to said handle assembly wherein said adaptor is secured to a distal end of said first handle member and holds said proximal end of said sheath between said first adaptor member and said second adaptor member, and wherein said adaptor is tapered downwardly in a distal direction to prevent said adaptor from being pulled out of said handle assembly.

* * * * *

UNITED STATES PATENT AND TRADEMARK OFFICE
CERTIFICATE OF CORRECTION

PATENT NO. :     5,234,460

DATED       :     August 10, 1993

INVENTOR(S) :    Albert E. Stouder, Jr.

It is certified that error appears in the above-identified patent and that said Letters Patent is hereby corrected as shown below:

In column 5, line 45, please change "applicant s" to --applicant's--.

In column 6, line 19, please change "which s" to --which is--.

In column 7, line 16, please change "sheath" to --distal--.

Signed and Sealed this

Eighth Day of March, 1994

Attest:

BRUCE LEHMAN

Attesting Officer     Commissioner of Patents and Trademarks